(12) United States Patent
Werner et al.

(10) Patent No.: US 6,385,477 B1
(45) Date of Patent: May 7, 2002

(54) METHOD FOR AUTOMATIZED DOSE PLANNING

(75) Inventors: Thomas Werner, Stockholm; Per Nylund, Huddinge, both of (SE)

(73) Assignee: Elektra AB, Stockholm (SE)

( * ) Notice: Subject to any disclaimer, the term of this patent is extended or adjusted under 35 U.S.C. 154(b) by 0 days.

(21) Appl. No.: 09/445,478

(22) PCT Filed: Jun. 18, 1998

(86) PCT No.: PCT/SE98/01201

§ 371 Date: Dec. 8, 1999

§ 102(e) Date: Dec. 8, 1999

(87) PCT Pub. No.: WO98/57705

PCT Pub. Date: Dec. 23, 1998

(30) Foreign Application Priority Data

Jun. 19, 1997 (SE) .............................................. 9702371

(51) Int. Cl.⁷ .................................................. A61B 5/05
(52) U.S. Cl. ....................... 600/407; 600/427; 606/130; 378/4; 378/64; 378/65; 703/2
(58) Field of Search .................................. 600/407, 411, 600/427, 166, 111; 424/9.4; 378/4, 64, 65, 108, 97; 250/370.07, 370.08, 370.09; 703/2

(56) References Cited

U.S. PATENT DOCUMENTS

| | | | |
|---|---|---|---|
| 5,027,818 A | * | 7/1991 | Bova et al. |
| 5,339,812 A | * | 8/1994 | Hardy et al. |
| 5,345,539 A | | 9/1994 | Webb |
| 5,458,125 A | * | 10/1995 | Schweikard |
| 6,125,295 A | * | 9/2000 | Cash, Jr. et al. |

* cited by examiner

Primary Examiner—Marvin M. Lateef
Assistant Examiner—Talaya G James

(57) ABSTRACT

A method and device are used for automatized dose planning in stereotactic radiosurgery. The method comprises the steps of: inputting into a computer location data on the target volume to be irradiated; positioning in the dose plan a number of shots having a preliminary weight, in certain preliminary positions in the target volume; and by an iterative minimizing method, minimizing the dose plan with respect to shot positions and shot weights.

10 Claims, 1 Drawing Sheet

METHOD FOR AUTOMATIZED DOSE PLANNING

This application is the national phase under 35 U.S.C. §371 of PCT International Application No. PCT/SE98/01201 which has an International filing date of Jun. 18, 1998, which designated the United States of America.

TECHNICAL FIELD

The present invention relates to a method for automatized dose planning in stereotactic radiosurgery.

BACKGROUND

In neurosurgical treatment of tumours, vascular deformities, and similar malformations in the brain, stereotactic radiosurgery techniques are often used, including for example gamma radiation from Cobolt-60 sources, such as the one commercially available under the denomination GammaKniven (Gamma Knife). Preferably, a plurality of sources of this kind are distributed around the head of the patient. By means of a collimator, the radiated beams are focused to a small spherical area in the brain. The diameter of the sphere is a matter of choice, as is also the duration of the radiation (weight), and by superposing within the brain the doses issued from several such irradiation points it becomes possible to produce a dose-radiation field wherein the dose received by the tumour is maximized while at the same time the dose received by surrounding tissue is minimized. Today, dose planning is effected entirely manually by physicians or hospital physicists who position radiation points, known as shots, inside the tumour and compare the dose distribution with the extension of the tumour by studying tomograms of the brain. It is likewise possible to seek assistance from a computer program, such as the commercially available GammaPlan program, which allows two or three dimensional viewing of target volumes and dose distribution as well as storage of lamina images of the brain that are obtained by imaging techniques such as computed tomography (CT), magnetic resonance imaging (MRI) and angiographic imaging, but wherein the choice of irradiation points is effected entirely manually. This essentially manual process is time-consuming and in addition places high demands on the experience and the skill of the individual performing the dose planning.

Attempts have also be made to effect dose planning by automated means. One such method was based on the idea of presuming the shots to be spheres with which one tried to fill the target volume optimally. This method functioned reasonably well as long as only two dimensions were involved but could not be applied to three-dimensional viewing. Another tested method involved continuous displacement of the shots through the target volume, to thus obtain a superposed dose which covered the target volume. This method functioned well in theory but has proved unsuccessful so far because it is not yet possible to continuously displace the shots through the volume.

OBJECT OF THE INVENTION

Consequently it is an object of the present invention to provide a method for automatized dose planning for stereotactic radiosurgery, by means of which the problems and disadvantages outlined above are completely or at least partly eliminated.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The enclosed drawing illustrates a flow chart relative to one embodiment of the method according to the invention.

DESCRIPTION OF PREFERRED EMBODIMENTS

Figure 1:
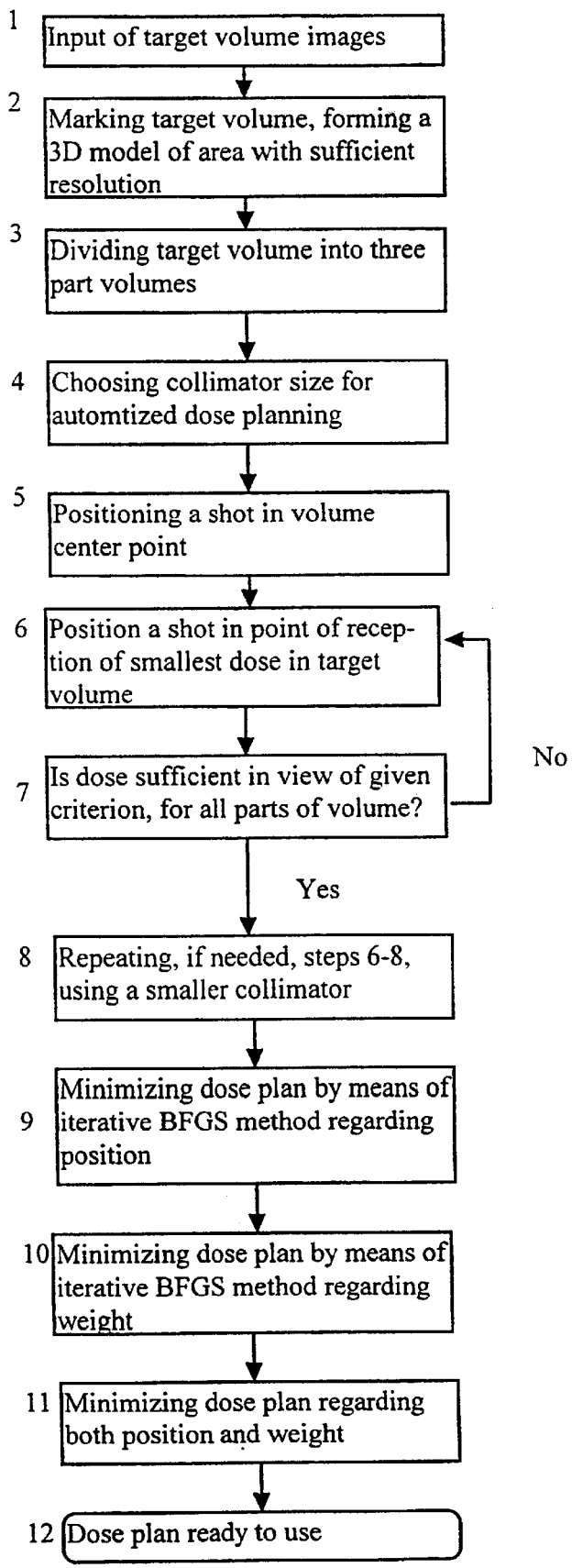

The method will be described in the following for exemplifying purposes in more detail by means of one example. The method comprises the following steps:

In a first step 1 anatomical images are inputted into the computer with the aid of the dose planning program. The images show clearly the target volume divided into thin laminae. In a second step 2, the target volume is marked by means of a drawing tool in the computer in order to thus provide information on the location of the target volume. On the basin of the data thus received the program produces a three-dimensional model of the target volume, with a predetermined resolution. This target volume is thereafter divided into three part volumes in step 3, viz.:

the interior volume;

the lamina volume immediately interiorly of the border of the target volume; and a volume built up around the area surrounding the target volume.

Thereafter, the configuration relating to the start of the dose planning is to be determined. Thus, in a first step 4 a collimator size is determined with respect to the first part of the automatized dose planning. The size is chosen in dependency of the size of the target volume. In a following step 5 the first shot is fired to the dose plan at the centre point of the target volume. The following shot is thereafter, step 6, set in a position in the interior volume, where the smallest dose is obtained. A test, step 7, is then performed in order to verify whether a dose meeting a criterion selected by the user is obtained in all of the interior volume. This criterion, which may be controlled by the user via the interface, could for instance be that 90% of the interior target volume is to have a dose above a predetermined value. If one finds, step 8, that the dose is insufficient, the process returns to step 6 above.

If needed, steps 6–8 are repeated, using a smaller collimator. In this manner it becomes possible to achieve an ideal dose distribution by means of a minimum number of shots, by setting the criterion at a low value when large collimators are positioned, and increasing it subsequently little by little while gradually smaller collimators are added.

Following this rough setting of the shots, improvements are made to the dose plan by use of an iterative method. A quality measure is used for the dose plan. The measure is obtained by including in the calculation thereof the dose received in the interior part, the shell part and the exterior part of the volume. Roughly speaking, a low dose is desirable exteriorly of the target volume, a high dose in the target volume interior, and uniformity in the shell volume. In a first optimization, step 9, a quasi-Newton method known as the Broyden-Fletcher-Goldfarb-Shannon method (BFGS method) is used in order to find a minimum in the multi-dimensional area formed by all shot positions. This method is known from other contexts and is described e.g. by W H Press, S A Tenkolsky, W T Vetterling and B P Flannery in "Numerical Recipes in C—The Art of Scientific Computing", Cambridge University Press, New York, USA. The number of dimensions thus becomes 3* (number of shots). The iteration continues until a sufficiently low measure is obtained. In this manner, the shots are displaced to positions that produce an improved dose plan. All shots still have the same weight, however.

A new sequence, step 10, of BFGS iterations is thereafter performed. This time only the weight factors are considered, however. Consequently, the shots are not displaced but the weight factors are adjusted in order to thus improve the dose plan.

A third search, step 11, for minima is then performed, and this time shot weight factors as well as shot positions are used in order to find the minimum. The shot weight factors and positions resulting from this third search step is thereafter verified by an operator. If the result is satisfactory, it is subsequently used in the dose plan for the treatment. If the operator is not satisfied, a supplementary manual optimisation is carried out in the conventional manner, during which several shots may be added, the shots may be displaced, and so on. The process is then restarted. This eliminates the risk that the optimization process gets stuck in non-optimum local minima. This iterative automatic optimization and the manual correction are repeated until the operator considers the results good enough to be used for the treatment.

The method thus functions by minimizing a function that describes the dose plan. This function is based on mean values and standard deviations in three different part volumes of the target volume to be irradiated. As already mentioned, these part volumes are the interior of the target volume, its border and its closest surrounding area. In order to permit the method both to improve over an already satisfactory dose plan and to create a satisfactory dose plan from a bad starting position, the function is divided into two parts.

In the following will be described one example of the setting of parameters to cover the target volume with 50% iso-doses. The first part serves to create a dose plan wherein the 50% iso-dose covers the target volume reasonably well, and the second part aims at ensuring that the 50% iso-dose tracks the target volume contours while at the same time the dose exteriorly thereof is minimized and the dose interiorly thereof is maximized. Preferably, the function is configured as follows:

$$f=f_1+f_2$$

wherein the part functions are:

$$f_1=k_1(0.5-m_r+1.28\sigma_r)+k_2(m_u+1.28\sigma_u-0.5)$$

$$f_2(1-M_i)+M_u+\sigma_r+|0.5-m_r|+k_3(0.3-m_r+1.28\sigma_r)$$

wherein $k_1=0$, if 90% of the volume in the interior of the target volume contains a dose exceeding 50% of the maximum dose, otherwise $k_1=100$, and wherein $k_2=0$, if 90% of the volume immediately externally of the target volume has a dose below 50% of the maximum dose, otherwise $k_2=100$. The fact that these constants are set to 100 is due to the fact that this part of the function is to be the dominant one when the above criteria are not met. Other values of these constants are, of course, also entirely possible and still give completely satisfactory results. In addition $k_3=0$, if 90% of the border of the volume has received a dose exceeding 30% of the maximum dose, otherwise $k_3=1$. Of the other constants, $m_i$ is the mean dose value in the interior of the volume and $\sigma_i$ is the standard deviation in the same area whereas $m_u$ and $\sigma_u$ designate the corresponding quantities of the area immediately exteriorly of the volume, and $m_r$ and $\sigma_r$ those of the border. The parameter values 0.5 in the functions above are derived from the choice of 50% iso-doses, and consequently will alter, should other choices be made.

It should be remembered, however, that the results of the optimization is but one suggestion for a dose plan and should always be evaluated by a responsible doctor or hospital physicist before application.

A condition for automatic positioning of the shots is that the radiation is spatially dependent. This is the case, however, for the majority of existing types of radiation, such as gamma radiation.

The method in accordance with the invention is suitable generally for automatized dose planning in stereotactic radiosurgery. The method is particularly suitable for use in connection with radiation equipment using several beam sources but having a fixed geometry, i.e. equipment the beam directions of which are fixed or at least locked in certain directions and consequently difficult to vary. In this type of equipment displacement of an isocenter consequently is impossible in the treatment room and instead the patient is moved relative to the isocenter, in order to obtain different isocenter positions. The method is suitable above all for use together with the commercially available Leksell Gamma Knife or similar equipment. The object of the method is to optimize the number of isocenters, beam dimensions and doses per isocenter on the basis of the known fixed beam directions. Owing thereto, the method may be used also in connection with arbitrary target geometries, irrespective of the complexity of the geometry.

The invention has been described above by means of one embodiment but it should be appreciated that several alternative varieties are possible. For instance, the number of part areas could exceed three. It is likewise possible to apply the dose-planning method to other forms of stereotactic radiosurgery than gamma radiation surgery. These and other obvious varieties must be considered to be within the scope of the invention such as the latter is defined in the appended claims.

What is claimed is:

1. A method for automatized dose planning in stereotactic radiosurgery, comprising the steps of:

inputting into a computer location data on a target volume to be irradiated;

positioning in the dose plan a number of shots having a preliminary weight, in certain preliminary positions in said target volume;

by an iterative minimizing method, minimizing the dose plan with respect to shot positions and shot weights; and dividing the volume into an interior, an intermediate and a surrounding pare volume, the interior part volume comprising an interior part of the target volume, the intermediate part volume comprising a layer immediately interiorly of a border of the target volume, and the surrounding part volume comprising an area surrounding the target volume, whereby the step of minimizing comprises separate optimization for the interior, intermediate and surrounding part volumes, in order to achieve a high dose in the target volume interior, a low dose in the surrounding volume, and uniformity in the intermediate volume.

2. The method as claimed in claim 1, wherein during the preliminary positioning, the shots are positioned in a center point of the target volume and in areas of least radiation in that volume, a sufficient number of shots being positioned to ensure that predetermined criteria are met.

3. The method as claimed in claim 1, wherein data inputting to the computer comprises the steps of inputting information on the volume to be treated by images, and on a basis of said information, forming a model of a target volume the position of which has been determined.

4. The method as claimed in claim 3, wherein the steps of inputting information include inputting laminar images.

5. The method as claimed in claim 1, wherein the minimizing step comprises a first minimization operation relative only to a position of the shots, a second minimization operation relative only to a weight of the shots, and a third minimization operation relative to the weights as well as to the positions of the shots.

6. The method as claimed in claim 1, wherein the minimization is effected by the Broyden-Fletcher-Goldfarb-Shannen method (BFGS).

7. The method as claimed in claim 1, wherein the data inputted into the computer are derived from lamina images of the brain produced by at least one of computed tomography, magnetic resonance imaging and angiographic imaging techniques.

8. The method as claimed in claim 1, wherein the intermediate part volume comprises a lamina of the border of the target volume.

9. A device for automatized generation of dose planning for stereotactic radiosurgery, comprising input means for inputting data relative to a position of the target volume to be irradiated, a memory for storing said data, and a data-processing unit adapted to position in a dose plan a number of shots having a preliminary weight in preliminary positions in said target volume, and to minimize said dose plan with respect to the positions and the weights of said shots by an iterative minimizing method, the data-processing unit further divides the volume into an interior, an intermediate and a surrounding part volume: the interior part volume comprising the interior part of the target volume, the intermediate part volume comprising the layer immediately interiorly of a border of the target volume, and the surrounding part volume comprising an area surrounding the target volume, whereby the minimizing comprises separate optimization for the interior, intermediate and surrounding part volumes, in order to achieve a high dose in the target volume interior, a low dose in the surrounding volume, and uniformity in the intermediate volume.

10. The device of claim 9, wherein the intermediate part volume comprises a lamina of the border of the target volume.

* * * * *